United States Patent [19]

Coan

[11] 4,229,540
[45] Oct. 21, 1980

[54] HYDROLASE PURIFIED FROM HUMAN PLASMA

[75] Inventor: Michael H. Coan, El Cerrito, Calif.

[73] Assignee: Cutter Laboratories, Inc., Berkeley, Calif.

[21] Appl. No.: 54,127

[22] Filed: Jul. 2, 1979

[51] Int. Cl.³ .................... C12N 9/48; C12N 9/50; C12N 9/14

[52] U.S. Cl. .................... 435/219; 435/195; 435/212; 435/2; 435/13; 424/94; 424/101

[58] Field of Search .................... 435/2, 13, 195, 212, 435/219; 424/101, 94

[56] References Cited

PUBLICATIONS

Kisiel et al., Biochemistry, vol. 16, No. 26, pp. 5824–5831 (1977).

*Primary Examiner*—Lionel M. Shapiro
*Attorney, Agent, or Firm*—James A. Giblin

[57] ABSTRACT

A previously undescribed hydrolytic enzyme has been successfully isolated from human plasma and purified to homogeneity. The enzyme has a molecular weight of about 70,000 daltons, has a Km for the substrate H-D-Phe-Pip-Arg-PNA of about 0.057 mM, a $K_I$ for benzamidine of about $1.1 \times 10^{-5}$ M, is bindable to and elutable from insoluble barium salts, is inhibited by antithrombin III, especially in the presence of heparin, and, in vitro, has been found to activate and degrade human Factor VIII, activate human Factor V, and inhibit platelet aggregation induced by ADP, epinephrine, or collagen, thus providing a substance useful for antithrombotic studies.

3 Claims, No Drawings

HYDROLASE PURIFIED FROM HUMAN PLASMA

BACKGROUND OF THE INVENTION

1. Field

This disclosure is concerned generally with a novel enzyme preparation and specifically with the preparation, characterization, and use of a hydrolytic enzyme which can be isolated from human plasma and has been found to have in vitro antithrombotic activity.

2. Prior Art

It is well known that a variety of hydrolytic enzymes can be found in human plasma and plasma fractions and it is known that the various steps in the blood clotting process are influenced and/or controlled by the presence or absence of certain enzymes and other substances. It has now been found that human plasma contains a previously unnoticed hydrolytic enzyme which demonstrates in vitro antithrombic activity. The preparation, characterization, and uses of this enzyme are disclosed in detail herein.

SUMMARY OF THE INVENTION

The enzyme preparation of this disclosure comprises a substantially homogeneous hydrolytic enzyme characterized by being obtainable from human plasma, having a molecular weight of about 70,000 daltons as determined by comparative polyacrylamide gel electrophoresis, having a Km for the substrate D-Phenylalanyl-L-Pipecolyl-L-Arginyl-p-nitroanilide (hereinafter designated H-D-Phe-Pip-Arg-PNA or S-2238 substrate, AB Kabi) of about 0.057 mM, having a $K_I$ for benzamidine of about $1.1 \times 10^{-5}$ M, being bindable to and elutable from insoluble barium salts, and, in vitro, demonstrating the properties of activating and degrading human Factor VIII, activating human Factor V, and inhibiting platelet aggregation induced by ADP, epinephrine, or collagen. The enzyme is further characterized in yielding, upon reduction, two peptide chains having respective molecular weights of about 25,000 and 45,000 daltons.

The enzyme may be prepared by subjecting human plasma to an alcohol precipitation step to yield an effluent which is then further processed by known techniques to form a human Factor IX concentrate which is then subjected to immobilized benzamidine (e.g. benzamidine-Sepharose) affinity chromatography followed by immobilized heparin (e.g. heparin-Sepharose) affinity chromatography to isolate the hydrolase.

The isolated and purified enzyme has been found useful in certain platelet aggregation studies and may in time be found to be therapeutically useful in treating coagulation disorders by inhibiting aggregation of platelets.

SPECIFIC EMBODIMENTS

The enzyme of this disclosure was discovered and characterized as a result of preliminary studies involving the role of Factor IX in thrombogenicity. In the examples below, a commercially available form of human Factor IX (Konȳne®, Cutter Laboratories, Inc.) was used as the starting material in isolating and purifying the enzyme.

Isolation and Purification: The general purification scheme, starting from human plasma can be illustrated as follows:

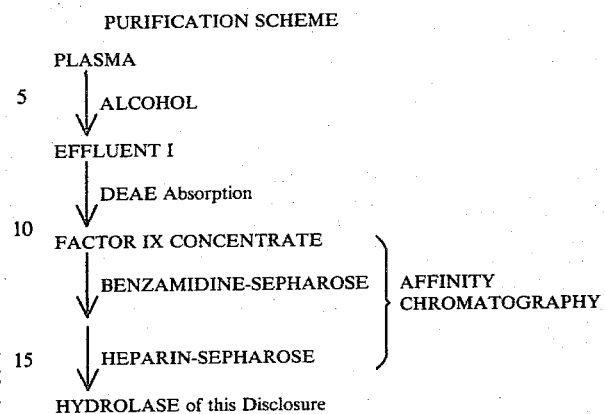

The specific purification steps involve obtaining Cohn Effluent I from cryosupernatant plasma using well known alcohol precipitation techniques. The Effluent I is then absorbed to DEAE Sephadex using known techniques, and the absorbed product is washed and eluted with 0.75 M ammonium bicarbonate, pH 7.6, at 5° C. The eluted material is lyophilized to a dry powder. The powder is then dissolved in an acetate buffer and subjected to affinity chromatography at 5° C. on a benzamidine Sepharose column as follows.

A benzamidine-Sepharose packing was prepared by coupling p-NH$_2$-benzamidine (with water soluble carbodiimide) to $\epsilon$-NH$_2$-caproic acid-Sepharose (prepared via known CNBr activation and coupling technique).

The benzamidine-Sepharose column (2.5×25 cm) was equilibrated with 0.025 M sodium acetate (pH 5.6). Sample was applied and the column was washed with 200 ml equilibration buffer. These fractions were discarded. Then a linear gradient (800 ml) to 0.3 M lysine in the acetate buffer was initiated (collect 8.0 ml fractions.

Activity of the enzyme was monitored using the chromogenic substrate H-D-Phe-Pip-Arg-PNA (S-2238, AB Kabi) and following the release of p-nitroanilide at 405 nm.

The active fraction, eluting at approximately 0.6 M NaCl was then pooled, concentrated, and dialyzed against an acetate buffer and chromatographed (affinity) at 5° C. as follows on a heparin-Sepharose prepared column prepared by coupling heparin to the Sepharose using known CNBr coupling techniques.

The heparin-Sepharose column (2.5×25 cm) was equilibrated with 0.025 M sodium acetate (pH 5.6), 0.1 M NaCl. Sample was applied, and the column was washed with 100 ml equilibration buffer, collecting 8.0 ml fractions. Then a linear gradient to 1.25 M NaCl in the acetate buffer was initiated. The total volume of the gradient was 800 ml.

Enzyme activity was again monitored by following the release of the p-nitroanilide (at 405 nm) from the S-2238 substrate. The active material, eluting at approximately 1.0 M NaCl, was pooled.

Attempts to isolate and purify the enzyme using polyhomoarginine-Sepharose and homoarginine-Sepharose affinity chromatography were unsuccessful since the enzyme bound so tightly it could not be eluted.

Characterization: About 10 mg of the enzyme was prepared from approximately 4 l of plasma using the above isolation and purification technique. Purity of the enzyme was shown by sodium dodecyl sulfate (SDS)

polyacrylamide gel electrophoresis (a single band resulted). Molecular weight was found to be about 70,000 daltons by comparison with standards.

Electrophoresis after reduction (with β-mercaptoethanol) showed two bands of peptide chains of lower molecular weight, 25,000 and 45,000 daltons, respectively.

The effects of inhibitors (see below) were determined using the S-2238 substrate. Other indicated substrates were used according to the manufacturer's (AB Kabi) directions.

Although the enzyme isolated in an active form hydrolyzes the S-2238 substrate at a rapid rate, it hydrolyzed other substrates available from AB Kabi (e.g. S-2251 is hydrolyzed to a slightly lesser extent, and S-2222, S-2302, and S-2160 about equally and much more slowly). $CaCl_2$ greatly enhances the enzymes activity. The enzyme was inhibited by antithrombin III especially in the presence of heparin, but poorly by soybean trypsin inhibitor or by diisopropylfluorophosphate. The enzyme bind to and can be eluted from insoluble barium salts. In vitro, the protein will activate and degrade human Factor VIII, will activate human Factor V, and will inhibit epinephrine-induced platelet aggregation; however, the in vivo function is unknown.

Further Characterizations: Some further physical-chemical characterization of the enzyme was done. The $K_m$ for the S-2238 substrate is 0.057 mM. The $K_I$ for benzamidine is $1.1 \times 10^{-5}$ M. The activity of the enzyme towards the S-2222 substrate (specific for Factor Xa) is poor. It hydrolyzes this substrate only 14% as fast as S-2238 substrate. Soybean trypsin inhibitor does not affect the hydrolysis of S-2238 substrate, and TLCK (N-α-tosyl-L-lysylchloromethane hydrochloride) at 0.1 mM inhibits only 25%. APB (p-amidino-phenacylbromide) at 1 mM inhibits 30% and at 3 mM, 60%.

Immunological studies have shown that antibody to prothrombin (Behring) does not inhibit the amidase activity. However, antiserum to the enzyme cross reacts with prothrombin. Immunoelectrophoresis of the enzyme clearly shows that the presence of heparin markedly changes the mobility.

In in vitro coagulation tests, the hydrolase activates and then begins to degrade human Factor V (in plasma). Bovine Factor V (in $BaSO_4$-absorbed plasma) is apparently activated. The effect of this enzyme on Factor VIII is questionable due to inconsistencies in the VIII$_t$ assay. These findings are summarized in Table III.

Earlier speculation proposed that the hydrolase was analagous to Bovine Protein C. Table I below shows a comparison of properties of the 2 enzymes.

TABLE I

Comparison of Present Hydrolase and Bovine Protein C*

| Present Human Hydrolase | Bovine Protein C |
|---|---|
| 2 Chain 45K, 25k | 2 Chain 41K, 21K |
| DFP-Poor Inhibitor | DFP-Readily Inhibits |
| AT-III - Inhibits | AT-III - No Effect |
| AT-III + Heparin - Better Inhibition | AT-III + Heparin - No Effect |
| STI - No Inhibition | STI - No Inhibition |
| CaCl$_2$ - Enhances Activity | CaCl$_2$ - Enhances Activity |
| EDTA - Kills Activity | EDTA - Removes Ca$^{2+}$ Effect |
| Activates Bovine Factor V | Destroys Bovine Factor V |
| Activates and Degrades Human Factors V and VIII | and not Human Factor V |

*As described by Kisiel et al, Biochemistry, 16 pp. 5824-30 (1977).

The relative activities of the present hydrolase and protein C against a variety of commercially available substrates (AB Kabi) also indicated differences.

TABLE II

Relative Activity of Hydrolase and protein C* Towards Several Chromogenic Substrates

| Substrate | Present Hydrolase | Protein C |
|---|---|---|
| S-2238 | 1.00 | 1.18 |
| S-2160 | 0.10 | 1.00 |
| S-2302 | 0.11 | 0.68 |
| S-2251 | 0.75 | 0.00 |
| S-2222 | 0.14 | 0.10 |

*as determined by Kisiel, et al, loc. cit.

The above differences appear to be enough to indicate that the present hydrolase is not "Human Protein C".

Other properties of the newly characterized hydrolase are summarized in Table III.

TABLE III

Other Properties of Present Hydrolase

Inhibited by Trasylol ®
No effect on fibrinogen (by SDS gels and clotting test)
No effect on plasminogen (by SDS gels and activity)
No effect on Factors II, VII, IX, X, XI, and XII
No effect on prekallikrein
Inhibits platelet aggregation
pH optimum 7.4 but unstable at alkaline pH

COAGULATION STUDIES AND USES

The effects of the present enzyme on coagulation factors were determined using standard coagulation assays in deficient plasmas and using plasma or commercial concentrates (e.g. Koāte ® or Konȳne ® plasma fractions, Cutter Laboratories, Inc.) as the source of the factor studies (see Table III).

Platelet aggregation studies were done with platelet rich plasma or washed platelets using a Payton dual channel Aggregometer.

The usefulness of the enzyme is illustrated by showing its effect on platelet aggregation, thus making it useful for further studies in that area.

For example, it was found that:

1. Platelet aggregation caused by 0.01 mg/ml collagen was inhibited by the present enzyme at 0.015 mg/ml.

2. A concentration of 0.001 mg/ml epinephrine caused platelet aggregation this could be inhibited by 0.008 mg/ml of the enzyme.

3. Platelet aggregation caused by 0.03 mg/ml of ADP was inhibited by 0.005 mg/ml of the enzyme.

The above findings clearly establish the utility of the enzyme as a research and possibly diagnostic tool.

I claim:

1. An enzyme preparation comprising a substantially homogeneous hydrolytic enzyme characterized by being obtainable from human plasma, having a molecular weight of about 70,000 daltons as determined by comparative polyacrylamide gel electrophoresis, having a $K_m$ for the substrate H-D-Phe-Pip-Arg-PNA of about 0.057 mM, having a $K_I$ for benzamidine of about $1.1 \times 10^{-5}$ M, being bindable to and elutable from insoluble barium salts, and, in vitro, capable of activating and degrading human Factor VIII, activating human Factor V, and inhibiting platelet aggregation induced by epinephrine, ADP, or collagen.

2. The enzyme preparation of claim 1 wherein the enzyme, upon reduction, yields two peptide chains having respective molecular weights of about 25,000 and 45,000 daltons.

3. A method of isolating a hydrolase enzyme as defined in claim 1 from human plasma which comprises the steps of a. passing a human Factor IX concentrate through an immobilized benzamidine affinity chromatography column;
b. eluting the product held thereby and collecting it to form a first isolation product;
c. passing the first isolation product through an immobilized heparin affinity chromatography column; and
d. eluting the product held thereby to isolate the enzyme.

* * * * *